(12) United States Patent
Corbett et al.

(10) Patent No.: US 10,520,412 B2
(45) Date of Patent: Dec. 31, 2019

(54) PARTICLE CHARACTERISATION

(71) Applicant: MALVERN PANALYTICAL LIMITED, Malvern, Worcestershire (GB)

(72) Inventors: Jason Corbett, Malvern (GB); Alex Malm, Malvern (GB)

(73) Assignee: Malvern Panalytical Limited, Malvern, Worcestershire (GB)

( * ) Notice: Subject to any disclaimer, the term of this patent is extended or adjusted under 35 U.S.C. 154(b) by 0 days.

(21) Appl. No.: 16/266,230

(22) Filed: Feb. 4, 2019

(65) Prior Publication Data
US 2019/0242805 A1 Aug. 8, 2019

Related U.S. Application Data

(63) Continuation of application No. 15/762,422, filed as application No. PCT/GB2016/052786 on Sep. 9, 2016, now Pat. No. 10,197,485.

(30) Foreign Application Priority Data

Sep. 23, 2015 (GB) .................................. 1516853.7
Jun. 20, 2016 (GB) .................................. 1610718.7

(51) Int. Cl.
*G01N 15/02* (2006.01)
*G01N 15/00* (2006.01)

(52) U.S. Cl.
CPC . *G01N 15/0211* (2013.01); *G01N 2015/0038* (2013.01); *G01N 2015/0053* (2013.01); *G01N 2015/0222* (2013.01)

(58) Field of Classification Search
CPC ....... G01N 15/0211; G01N 2015/0038; G01N 2015/0222; G01N 2015/0053
(Continued)

(56) References Cited

U.S. PATENT DOCUMENTS 4,473,296 A * 9/1984 Shofner ................. G01N 21/53
356/336
4,710,025 A 12/1987 Wyatt et al.
(Continued)

FOREIGN PATENT DOCUMENTS

| EP | 1291642 A1 | 3/2003 |
|---|---|---|
| EP | 2365313 A1 | 9/2011 |

(Continued)

OTHER PUBLICATIONS

Extended European Search Report dated Sep. 22, 2017, directed to European Application No. 17162676.5; 11 pages.
(Continued)

*Primary Examiner* — Roy M Punnoose
(74) *Attorney, Agent, or Firm* — Morrison & Foerster LLP

(57) ABSTRACT

Disclosed herein is a method of characterizing particles in a sample. The method comprises illuminating the sample in a sample cell with a light beam, so as to produce scattered light by the interaction of the light beam with the sample; obtaining a time series of measurements of the scattered light from a single detector; determining, from the time series of measurements from the single detector, which measurements were taken at times when a large particle was contributing to the scattered light; determining a particle size distribution, including correcting for light scattered by the large particle.

20 Claims, 10 Drawing Sheets

(58) Field of Classification Search
USPC .......................................................... 356/336
See application file for complete search history.

(56) References Cited

U.S. PATENT DOCUMENTS

| | | | |
|---|---|---|---|
| 6,016,195 A | 1/2000 | Peters | |
| 6,052,184 A | 4/2000 | Reed | |
| 8,854,621 B1* | 10/2014 | Muschol | G01N 21/47 |
| | | | 356/336 |
| 2007/0229823 A1* | 10/2007 | Sung | G01N 15/1463 |
| | | | 356/336 |
| 2008/0221814 A1* | 9/2008 | Trainer | G01B 11/08 |
| | | | 702/70 |
| 2013/0218519 A1* | 8/2013 | Tochino | G01N 15/0211 |
| | | | 702/157 |
| 2014/0226158 A1* | 8/2014 | Trainer | G02B 6/32 |
| | | | 356/336 |
| 2019/0078990 A1 | 3/2019 | Corbett | |

FOREIGN PATENT DOCUMENTS

| | | |
|---|---|---|
| EP | 3379232 A1 | 9/2018 |
| WO | 96/22521 A1 | 7/1996 |
| WO | 2008/092272 A1 | 8/2008 |
| WO | 2009/090562 A2 | 7/2009 |
| WO | 2012/172330 | 12/2012 |
| WO | 2017/051149 A1 | 3/2017 |
| WO | 2018/172362 A1 | 9/2018 |

OTHER PUBLICATIONS

International Search Report and Written Opinion dated May 17, 2018, directed to PCT Application No. PCT/EP2018/057033; 17 pages.
International Search Report and Written Opinion dated Jan. 12, 2016, directed to PCT Application No. PCT/GB2016/052786; 9 pages.
Zhu et al., "Analysis of Noisy Dynamic Light Scattering Data Using Constrained Regularization Techniques," Applied Optics 51(31): pp. 7537-7548.
"Zetasizer Nano Series," (Aug. 2009) User Manual published by Malvern; 308 pages.
International Search Report and Written Opinion dated Jun. 19, 2017, directed to International Application No. PCT/GB2017/050733; 13 pages.
International Search Report and Written Opinion dated Oct. 9, 2009, directed to International Application No. PCT/IB2009/005020; 10 pages.

* cited by examiner

PARTICLE CHARACTERISATION

CROSS-REFERENCE TO RELATED APPLICATIONS

This application is a continuation application of U.S. application Ser. No. 15/762,422 filed Mar. 22, 2018, which is a national stage application under 35 USC 371 of International Application No. PCT/GB2016/052786, filed Sep. 9, 2016, which claims the priority of GB App. No. 1516853.7, filed Sep. 23, 2015 and GB App. No. 1610718.7 filed Jun. 20, 2016, the entire contents of which are incorporated herein by reference.

FIELD OF THE INVENTION

The invention relates to a particle characterisation instrument, and to a method of particle characterisation, which may include adaptive photon correlation spectroscopy.

BACKGROUND OF THE INVENTION

Photon correlation spectroscopy (also termed dynamic light scattering, or DLS) is a technique for characterising particles by the temporal variation in the intensity of light scattered from a region of the sample. A time series of measurements of scattered light is used to determine a size or size distribution of particles dispersed in the sample.

As discussed in WO2009/090562, it is well known that the intensity of light scattered by particles smaller than the wavelength of the illuminating light is a strong function of particle size. In the Rayleigh scattering limit, where particle radius is below 0.1 of the wavelength of the illuminating light, the intensity of scattered light is proportional to the sixth power of the particle radius. The light scattered from such small particles is also substantially isotropic. Therefore in a dispersion of proteins, typically of size 0.3 nm-20 nm, an aggregate or filter spoil particle, e.g. >100 nm in size, may dominate the signal until it has diffused away from the optical detection volume within the sample. In the often used Cumulants reduction, the output of Z average and polydispersity index (Pdi), may be badly skewed by the larger fraction.

This sensitivity to 'dust' is known, with many literature sources stressing the importance of careful sample preparation, however the presence of filter spoil or aggregates is difficult to avoid completely.

A light scattering measurement on a sample containing primarily small particles and also larger particles can be very sensitive to the larger particles, or even to individual large particles. The larger particles can degrade the quality with which the smaller particles can be characterised. Such larger particles may be unwanted contaminants: they may be aggregates of the primary particles, or some other material.

WO2009/090562 proposes addressing this problem by use of multiple photon counting detectors. A supplemental detector at a low scattering angle is proposed to detect when a larger particle is scattering light, and then data from a detector intended for DLS analysis can be ignored when larger particles are present.

Although this represents a significant advance, shortcomings still remain, and an improved method and apparatus for DLS is desirable.

It is also known to perform particle characterisation by analysing a pattern of diffracted/scattered light from a sample. The light source is generally a laser, and this type of analysis may sometimes be referred to as laser diffraction analysis or Static Light Scattering (SLS). Large particles may also be a problem in static light scattering measurements: scattering from larger particles may obscure relatively small amounts of light scattered from smaller particles.

To the extent that prior art methods consider the problem of contaminants, data that includes scattering from contaminants is simply discarded. The consequence of this crude approach is that data may be wrongly discarded, and as a consequence incomplete results may be presented, or longer run times may be necessary to obtain sufficient valid data.

Methods and apparatus that facilitate reliable analysis of polydisperse particles are desirable.

According to a first aspect of the invention, there is provided a method of characterising particles in a sample, comprising: illuminating the sample in a sample cell with a light beam, so as to produce scattered light by the interaction of the light beam with the sample; obtaining a time series of measurements of the scattered light from a single detector; determining, from the time series of measurements from the single detector, which measurements were taken at times when a large particle was contributing to the scattered light; and determining a particle size distribution from the time series of measurements, including correcting for light scattered by the large particle.

SUMMARY OF THE INVENTION

According to another aspect of the invention, there is provided a method of characterising particles in a sample, comprising: illuminating the sample in a sample cell with a light beam, so as to produce scattered light by the interaction of the light beam with the sample; obtaining a time series of measurements of the scattered light from a single detector; determining, from the time series of measurements from the single detector, which measurements include unusual data; and determining a particle size distribution from the time series of measurements, including correcting for unusual data. The unusual data may be identified with reference to a rejection/segregation criteria. Correcting for the unusual data may comprise excluding or segregating (and potentially separately analysing) the measurements including the unusual data.

In another aspect, the time series of measurements may be obtained from more than one detector. Determining which measurements were taken at a time when a large particle was contributing to scattered light may comprise using measurements from more than one detector. Determining a particle size distribution may be done from a time series of measurements from more than one detector.

Correcting for light scattered by the large particle may comprise processing the time series of measurements.

Determining a particle size distribution may comprise performing a dynamic light scattering correlation operation on the processed time series of measurements.

Determining a particle size distribution may comprise performing a light diffraction particle characterisation analysis (for example using Fraunhofer or Mie scattering theory) on the time series of measurements. The methods disclosed herein may be applied to Static Light Scattering (SLS), Dynamic Light Scattering (DLS), Electrophoretic Light Scattering (ELS), Magnetophoretic Light Scattering (MLS) and related methodologies, for instance to measure protein mobility, surface zeta, microrheology etc. Correlated light scattering data could be processed for microrheology measurements, with transient effects removed in a manner to the other embodiments described herein.

There may be a plurality of large particles, and the method may comprise correcting for light scattered by the large particles. The term "large particle" does not exclude a plurality of large particles. The term "large particle" may mean a particle with a diameter larger than a predetermined threshold size. The term "large particle" may be substituted herein with "unusual particle". In some embodiments, it is simply unusual (or transient) scattering data that is identified/corrected for, for instance based on an analysis (e.g. statistical analysis) of a parameter determined with reference to the data.

In some embodiments, correcting for light scattered by the large particle comprises excluding the measurements taken at times when the large particle was contributing to the scattered light. The remaining data may subsequently be, for example, concatenated or zero-padded, to form a continuous set of data.

In other embodiments, correcting for light scattered by the large particle comprises determining a model of the light scattered by the large particle; and removing the model from the measurements. For example, a model may be fitted to the measured time series to determine the part of the measured time series that is due to scattering from a large particle. This model may then be removed from the measured data, for example the model may be subtracted or deconvoluted from the measured data. The model may be fit to, and removed from, the measured time series data or processed data such as the output of the dynamic light scattering correlation operation.

In some embodiments, measurements taken at times when a large particle was contributing to the scattered light may be processed separately from measurements taken at times when a large particle was not contributing to the scattered light, so as to separately characterise larger particles and smaller particles. The accuracy of a laser/light diffraction analysis may be improved by separately analysing measurements when large particles are present.

Other embodiments may use a combination of the above methods for correcting for light scattered by the large particle.

By correcting for the signal due to scattering from large particles in this way, more accurate information about the small particles present in a sample can be extracted from DLS measurements without requiring multiple photon counting detectors. Fitting a model of large particle behaviour to the data and removing the estimated contribution of the large particle from the data may be particularly advantageous, as at least a substantial part of small particle data is not lost from those times during which a large particle dominated the measured signal.

In some embodiments, determining which measurements were taken at times when a large particle was contributing to the scattered light may comprise detecting a low frequency variation in the time series of measurements, the low frequency variation corresponding with a large particle.

In some embodiments, large particles that are contaminants may be identified as such by their low frequency contribution to scattering.

Alternatively or additionally, determining which measurements were taken at times when a large particle was contributing to the scattered light may comprise determining period of time during which the measurement exceeds a threshold value of light intensity.

In some embodiments, determining which measurements were taken at times when a large particle was contributing to the scattered light may comprise dividing the time series up into a plurality of shorter sub-runs, and then determining which of the sub-runs comprise measurements with a scattering contribution from a large particle.

In these embodiments, determining which of the sub-runs comprise measurements with a scattering contribution from a large particle may comprise evaluating whether the measurement within each sub-run exceeds a threshold value of light intensity, or whether the average measurement over each sub-run exceeds a threshold value of light intensity.

Alternatively, determining which of the sub-runs comprise measurements with a scattering contribution from a large particle may comprise detecting low frequency variations in a measurement within a sub-run.

In some embodiments, determining which of the sub-runs comprise measurements with a scattering contribution from a large particle may comprise: performing a correlation on each sub-run.

Performing a correlation on each sub-run may comprise determining a polydispersity index (Pdi), a particle size distribution or a Z-average mean particle size for each sub-run by dynamic light scattering. Each sub-run may preferably be analysed using the cumulants method, but other methods can also be used, such as the CONTIN method, or maximum entropy method. The processing of the time series of measurements so as to correct for light scattered by the large particle may comprise correcting for a background in the sub-runs in which a large particle was identified by the correlation. The processing of the time series of measurements so as to correct for light scattered by the large particle may comprise excluding the measurements taken at times (e.g. sub-runs) when the large particle was contributing to the scattered light.

Determining which sub-runs include measurements were taken at times when a large particle was contributing to scattering may comprise comparing a parameter calculated from each sub-run with a threshold value of the same parameter.

The threshold value may be determined from a distribution of the parameters calculated for each sub-run. Sub-runs where the parameter is a statistical outlier may be discarded or segregated for separate analysis.

The threshold value of the parameter may be derived from an average value of the same parameter calculated from all the sub-runs. The threshold value may be derived from the standard deviation and average value of the parameter. The threshold value may be determined by adding 2, 3, 4, 5, or 6 standard deviations to the average parameter value.

The parameter may comprise: Z average, Pdi, average intensity, the drift and/or spread in measured intensity over each sub-run, and/or Doppler frequency width.

The average value of the parameter may be calculated from a best fit to a distribution or histogram of the parameters calculated for each sub-run. The best fit may have a normal distribution.

The rejected or segregated data (e.g. sub-runs) may be separately analysed to characterise the large particle(s). This may help identify the nature of aggregates, dust and/or contaminants in the sample.

In some embodiments in which the time series is divided into sub-runs, each sub-run may have a duration of: 5 seconds or less; 2 seconds or less; 1 second or less; 0.5 seconds or less; or 0.1 seconds or less.

The method may comprise using at least 10, 20, 50 or 100 sub-runs to characterise a sample.

In some embodiments of the method according to the first aspect of the invention, the predetermined size may be selected from: 1000 μm, 500 μm, 100 μm, 20 μm, 5 μm, 1 μm, 300 nm 100 nm, and 50 nm.

Determining a particle size distribution from the processed time series of measurements, including correction for light scattered by the large particle, may comprise analysing each sub-run (that has not been discarded as including a contribution of scattered light from a larger particle) separately, and then using the average of each sub-run analysis to determine the particle size distribution. For example, in the case of a DLS measurement, the correlograms of each sub-run could be averaged, and the particle size distribution determined from the averaged correlogram.

The method may comprise performing an initial number of sub-runs, with further sub-runs being recorded and added to the preceding data until an average obtained from the combined data has converged (e.g. until the average correlogram has converged). A convergence criteria may be based on the amount that the average obtained from the combined data changes over a number of succeeding measurements.

In general terms, a criteria identifying a scattering contribution from a large particle may be based on a parameter determined from the time series of measurements of scattered light. The use of such a dynamic criteria for categorising particles as unusual or large means that the method can be robust enough to include scattering data from large particles when this is appropriate, for example in the case of a highly polydisperse and variable sample, and to exclude or correct for scattering from large particles when it is appropriate, for example to reject contaminants or aggregates in a less polydisperse sample.

In some embodiments the threshold used to determine which data is rejected/segregated may be user selectable. Information (e.g. statistical information, a distribution of a parameter and/or analysis results obtained using the threshold) may be presented to the user to help the user make a selection of the appropriate threshold.

According to a second aspect of the invention, there is provided an apparatus for characterising particles in accordance with the method of any other aspect or embodiment this disclosure, comprising: a light source, a sample cell, a detector and a processor; wherein the light source is operable to illuminate a sample within the sample cell with a light beam so as to produce scattered light by interactions of the light beam with the sample; the detector is configured to detect the scattered light and produce a time series of measurements; the processor is configured to receive the time series of measurements, and determine, from the time series of measurements from a single detector, which measurements were taken at times when a large particle was contributing to the scattered light; determine a particle size distribution by performing a dynamic light scattering correlation operation on the processed time series of measurements, including correcting for a light scattered by the large particle.

According to a third aspect of the invention, there is provided an apparatus for characterising particles in accordance with the method of any aspect or embodiment of this disclosure, comprising: a light source, a sample cell, a detector and a processor; wherein the light source is operable to illuminate a sample within the sample cell with a light beam so as to produce scattered light by interactions of the light beam with the sample; the detector is configured to detect the scattered light and produce a time series of measurements; the processor is configured to receive the time series of measurements, and determine, from the time series of measurements from the detector, which measurements were taken at times when a large particle was contributing to the scattered light; determine a particle size distribution from the processed time series of measurements, including correcting for light scattered by the large particle.

In some embodiments of the apparatus, correcting for light scattered by the large particle comprises excluding the measurements taken at times when the large particle was contributing to the scattered light. In alternative embodiments, correcting for light scattered by the large particle comprises determining a model of the light scattered by the large particle; and removing the model from the measurements. In some embodiments, measurements taken at times when a large particle was contributing to the scattered light may be processed separately from measurements taken at times when a large particle was not contributing to the scattered light, so as to separately characterise larger particles and smaller particles.

In some embodiments the detector may comprise a photon counting detector, and/or may be configured to detect backscattered light. The apparatus may comprise a plurality of detectors configured to detect the scattered light.

The apparatus may further comprise an optical fibre that provides an optical path between the detector and a scattering volume that is illuminated by the light source.

Features of each and every aspect may be combined with those of each and every other aspect.

BRIEF DESCRIPTION OF THE DRAWINGS

Example embodiments will be described, purely by way of example, with reference to the accompanying drawings, in which.

DETAILED DESCRIPTION OF THE INVENTION

Figure 1:
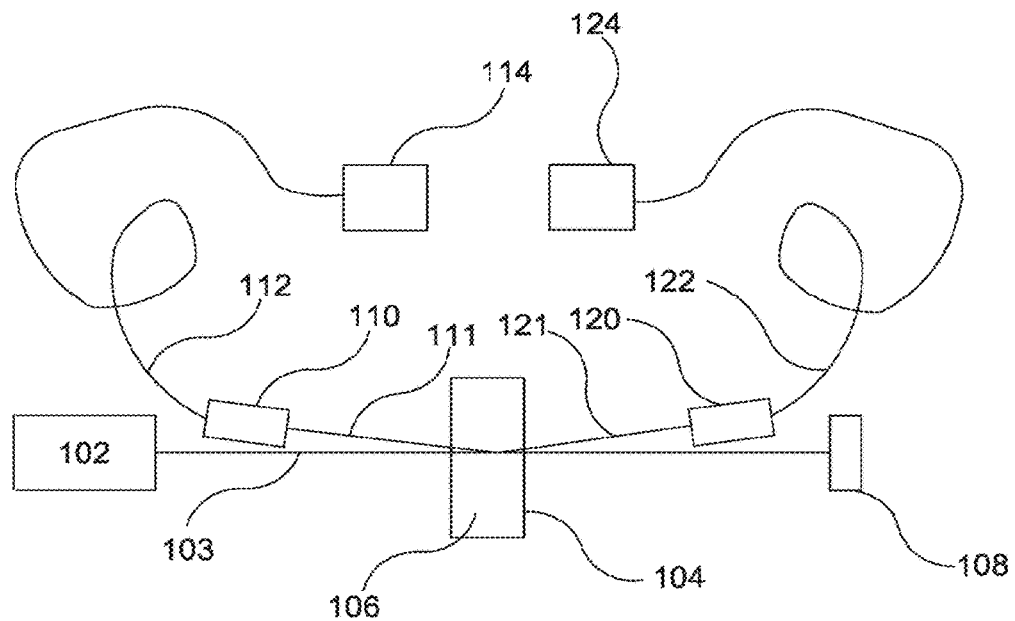
FIG. 1 is a schematic of a particle characterisation apparatus according to an embodiment.

FIG. 1 shows a particle characterisation apparatus comprising a light source 102, sample cell 104, backward scatter detector 114, forward scatter detector 124, and light trap 108.

The light source 102 may be a coherent light source, such as a laser, and may output mono-chromatic light. Alternatively, the light source 102 may be an LED. The light source 102 is configured to illuminate a sample 106 within the sample cell 104 with a light beam 103 along a light beam axis.

The interaction of the illuminating light beam 103 with the sample 106 produces scattered light. Forward scattered light 121 may be defined as light that is scattered at angles of less than 90 degrees to the direction of the illuminating light beam axis. Backward scattered light 111 may be defined as light that is scattered at angles of more than 90 degrees to the direction of the light beam axis (i.e. having a direction component in the opposite direction to the illuminating light beam).

The forward scatter detector 124 is configured to detect forward scattered light 121. The forward scattered light 121 is directed to the detector 124 via a collecting lens 120, which couples the scattered light 121 to an optical fibre 122. The optical fibre 122 provides an optical path to the forward scatter detector 124. The collecting lens 120 may be a graded refractive index lens, or any other suitable lens. Further, or fewer optical components may be included in the optical path between the illuminated region of the sample 106 and the forward scattering detector 124. For instance, in some embodiments, the optical fibre 122 may be omitted, and free space optics used instead.

The backward scatter detector 114 is configured to detect backward scattered light 111. The backward scattered light 111 is directed to the sensor via a collecting lens 110, which couples the scattered light 111 to an optical fibre 112. The optical fibre 112 provides an optical path to the backward scatter detector 114. The collecting lens 110 may be a graded refractive index lens, or any other suitable lens. Further, or fewer optical components may be included in the optical path between the illuminated region of the sample 106 and the backward scattering detector 114. For instance, in some embodiments, the optical fibre 112 may be omitted, and free space optics used instead.

In some embodiments, only a single detector may be provided, for instance only a side scattering detector (detecting light scattered at 90 degrees), or only a forward scattering detector, or only a backward scattering detector may be present.

The apparatus of FIG. 1 may be configured to perform a dynamic light scattering analysis, for instance using the output from a single detector (such as the backward scattering detector 114).

Figure 2:
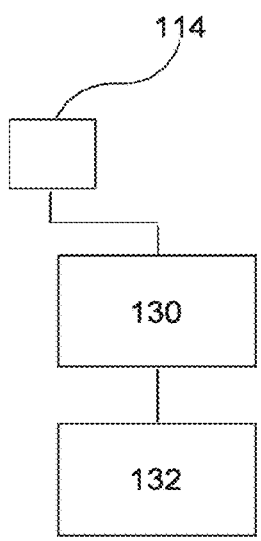
FIG. 2 is a schematic of a particle characterisation apparatus processing means according to an embodiment.

FIG. 2 shows detector 114, processor 130 and output device 132. The processor 130 is configured to receive a time series of light intensity measurements from the detector 114, and to perform a correlation operation on the measurements to characterise particles of a sample by dynamic light scattering. The processor 130 may store the measurements in a machine readable storage medium, for example in memory, on a solid state storage drive, a hard disk, in the cloud etc. The processor 130 may then output the results of the analysis to the output device 132, which may comprise a display screen.

The processor 130 is configured to determine, from a time series of measurements from a single detector 114, which measurements were taken at times when a large particle was contributing to the scattered light. This ability of the processor 130 to detect scattering from larger particles from a time series of measurements from a single detector is in contrast to the prior art, which relies on measurements from a supplemental detector (e.g. a forward scattering detector). The term large particle may mean a particle with diameter greater than a predetermined threshold size, or may refer to a particle that is a statistical outlier. The predetermined size may be user selectable, and may be: 50 nm, 75 nm, 100 nm, 150 nm. 200 nm, 300 nm, 500 nm.

Figure 3:
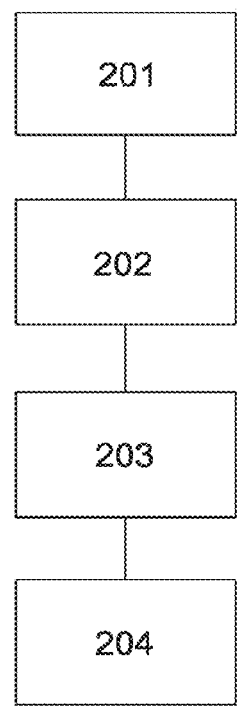
FIG. 3 is a flow diagram of a method according to an embodiment.

Apparatus according to an embodiment may combine the features shown in FIGS. 1 and 2 (and described with reference to these Figures), and may be configured to perform the method which is shown in outline form in FIG. 3.

FIG. 3 shows a series of method steps 201-204. Step 201 comprises illuminating a sample 106 in a sample cell 104 with a light beam 103, so as to produce scattered light 111 by the interaction of the light beam 103 with the sample 106.

Step 202 comprises obtaining a time series of measurements of the scattered light 111 from detector 114, which may be a single detector. The term "single detector" as used herein may include a plurality of detectors (e.g. a 1D or 2D detector element array) corresponding with a specific light scattering angle (or narrow range of light scattering angles, such as 5 degrees or less).

Step 203 comprises determining from the time series of measurements from the detector 114, which measurements were taken at times when a large particle (or large particles), with diameter greater than a predetermined threshold size, was contributing to the scattered light. A number of different methods can be used to do this, as will be explained more fully below.

Step 204 comprises determining a particle size distribution by performing a dynamic light scattering correlation operation on the time series of measurements, including correcting for a light scattered by the large particle (or large particles) in the measurements during periods in which a large particle was contributing to the scattered light. Removing this background scattered light from the large particle from the measurements may improve the quality and/or accuracy of the characterisation of the particles by DLS, because the relatively intense scattering from the larger particles will thereby be prevented from corrupting the characterisation of smaller particles within the sample (which may be the particles of most interest).

Figure 4:
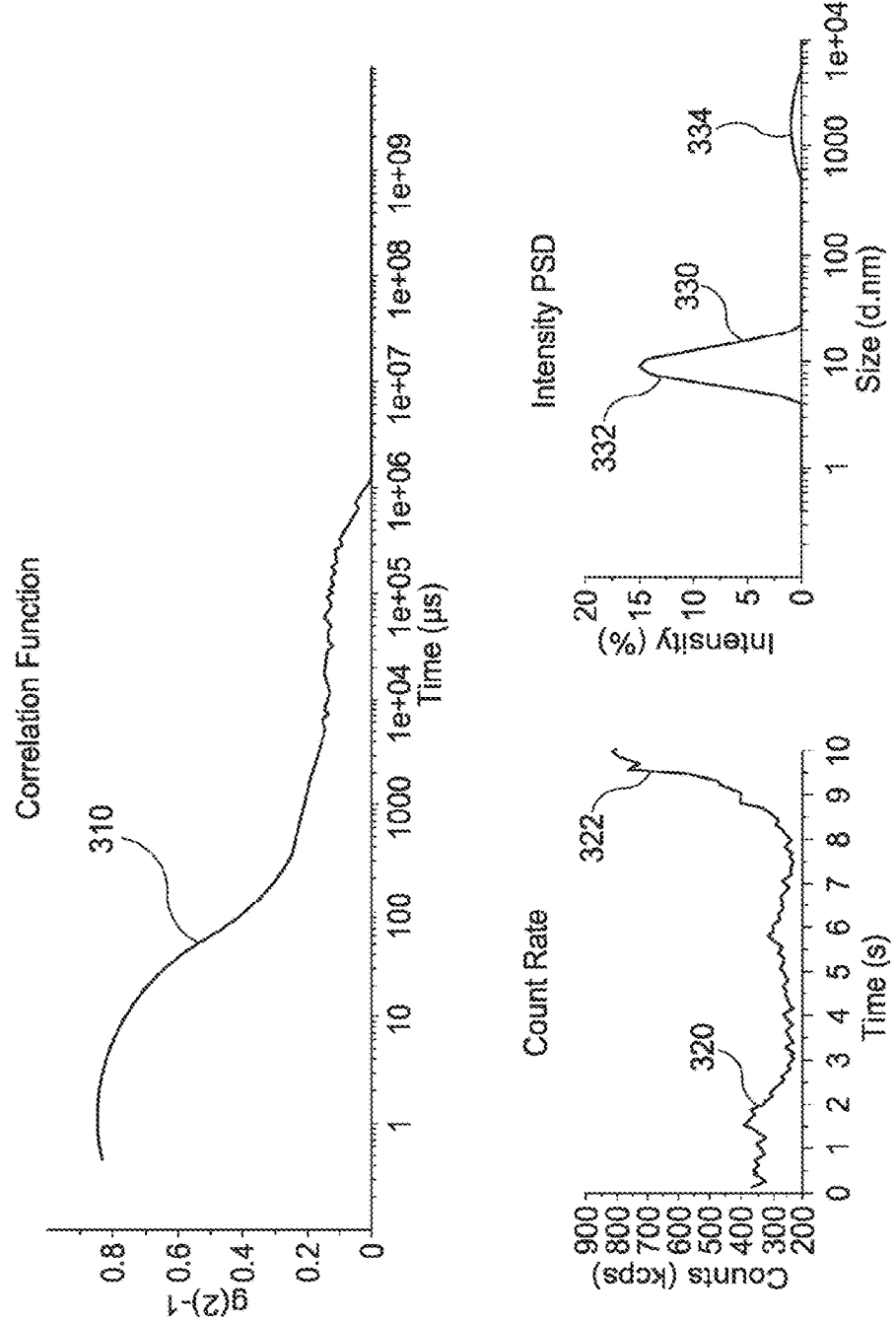
FIG. 4 shows some example results, for processing according to an embodiment.

FIG. 4 illustrates a time series of measurement results from a detector 320, along with a plot of a correlation function 310 obtained from the measurement results 320. A particle size distribution (PSD) plot 330 of scattered light intensity with respect to particle size is also shown. Examination of the measurements 320 shows that the light intensity markedly increases after t=8 s, corresponding with scattering from a large particle.

This is one way to identify measurements that are taken at times when a large particle is scattering light. In the present case, for example, a threshold intensity value of 600 counts per second could be used to identify light scattering from a large particle. Data within a predetermined time (e.g. is or 0.5 s) of this threshold being exceeded may be excluded from a subsequent DLS analysis. For example, if the threshold is exceeded at t=9 s, data from t=8 s onwards may be excluded, or a fitted model of the background due to the large particle removed from the these data. The precise values of intensity threshold and time window may depend on the instrument configuration and the specific measurement setup. The threshold may be 2, 3, 4, or 5 standard deviations of the intensity values (which may be determined after a complete measurement has been taken, or dynamically, as the measurement is taken).

Alternatively, or additionally, the frequency of features within the time series of measurements may be used to identify light scattering from a large particle: a low frequency feature is likely to correspond with a large particle. In the example data 320 the measurement is relatively stable, until the low frequency, large amplitude excursion from t=8 s. The combination of low frequency and large amplitude fluctuations in light intensity may be particularly characteristic of large particles, and may be used to identify times when a large particle is scattering. A frequency of less than 10, 5, 4, 3, 2, 1, or 0.5 Hz or less may be associated with a large particle.

The PSD plot 330 is based on processing the full time series of data, including the time series between t=8 s and t=10 s. It shows a light intensity peak corresponding with a particle size of around 1000 nm.

One way to identify that a large particle is present within a particular time window is to partition the full time series of data (or run) into a plurality of smaller duration periods or sub-runs, and then to perform a dynamic light scattering analysis on each of the sub-runs. For example, if the data 320 were partitioned into a plurality of sub-runs of duration 1 second, and a DLS correlation analysis performed on the data of each sub-run, it would be straightforward to identify in which sub-run a significant amount of light scattering is contributed by a large particle or particles (e.g. more than 1%, 5% or 10% of the total scattered light, or when the intensity PSD exceeds 1, 5 or 10% at a particle size over a specific threshold). The sub-runs with a significant amount of scattering from larger particles may then be excluded from the measurement series. The remaining measurement data may then be combined, and a DLS measurement performed based on the combined remaining data. Alternatively, a model of the background due to the large particle may be fitted to the data within each sub-run with a significant amount of scattering from larger particles. The estimate of the scattering signal due to the large particle, as calculated by the fitted model, may then be removed from the data within the sub-run. The remaining corrected data may then be combined with the data from the other sub-runs in the measurement series, and a DLS measurement performed on the combined corrected data series.

Embodiments of the invention may provide significantly improved DLS characterisation fidelity in cases where large particles are problematic.

Figure 5:
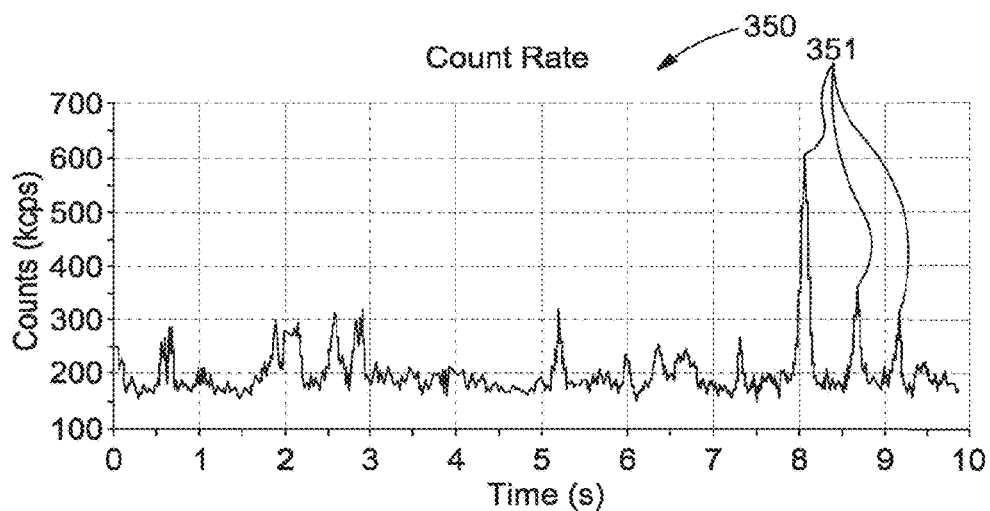
FIG. 5 shows a graph of photon count intensity over time, obtained from a poor quality sample in which spikes are present in the data, as a result of scattering from highly scattering particles.

FIG. 5 shows a graph 350 of photon count rate over time obtained from a scattered light detector. Spikes 351 are present in the data (not all of which are labelled in FIG. 5), corresponding with periods of time when a highly scattering particle (i.e. a contaminant) is within the measurement volume of the instrument. One way to deal with this contribution from contaminants is to reject data when the contaminant is scattering light: to remove data during the periods corresponding with the spikes 351.

Figure 6:
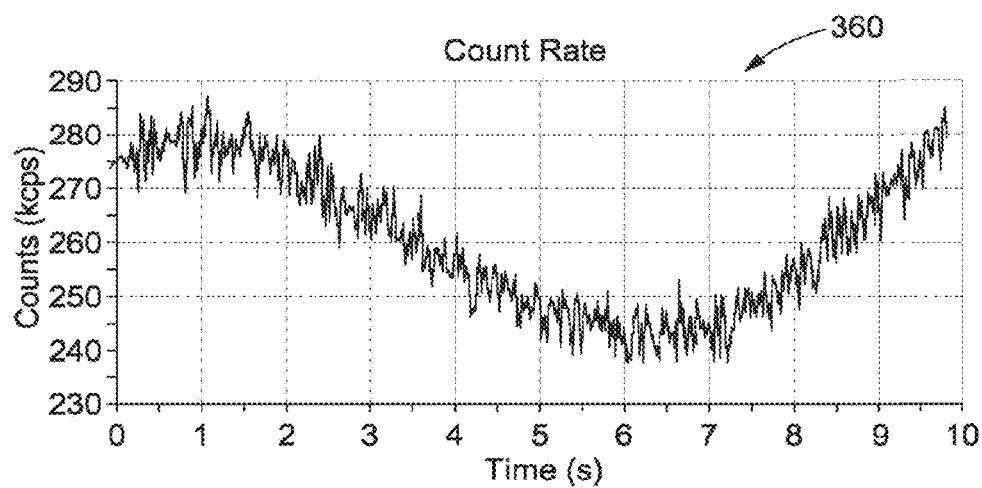
FIG. 6 shows a graph of photon count intensity over time, obtained from a poor quality sample in which a large particle causes a slow fluctuation in the data.

FIG. 6 shows a graph 360 of photon count rate over time obtained from a scattering detector. In contrast to the short duration "spikes" of FIG. 5, the contaminant for the data of FIG. 6 is a large particle that slowly impinges on the measurement volume, resulting in a low frequency variation in detected intensity. This type of contribution to scattering from a larger particle may be dealt with by removing the low frequency component of the data.

It is desirable to be able to identify sub-runs in which larger particles contributed to scattering. One way to do this is by determining intensity of each sub-run, and using an average intensity value (e.g. mean, median value etc) as a rejection criteria. Larger particles are associated with stronger scattering, so higher intensity sub-runs may be associated with larger particles. The threshold for rejection of sub-runs may be determined from the ensemble characteristics of all the sub-runs. For instance the threshold average intensity could be derived from an average intensity taken across all sub-runs (e.g. two or three standard deviations from an average intensity for all sub-runs).

Figure 7:
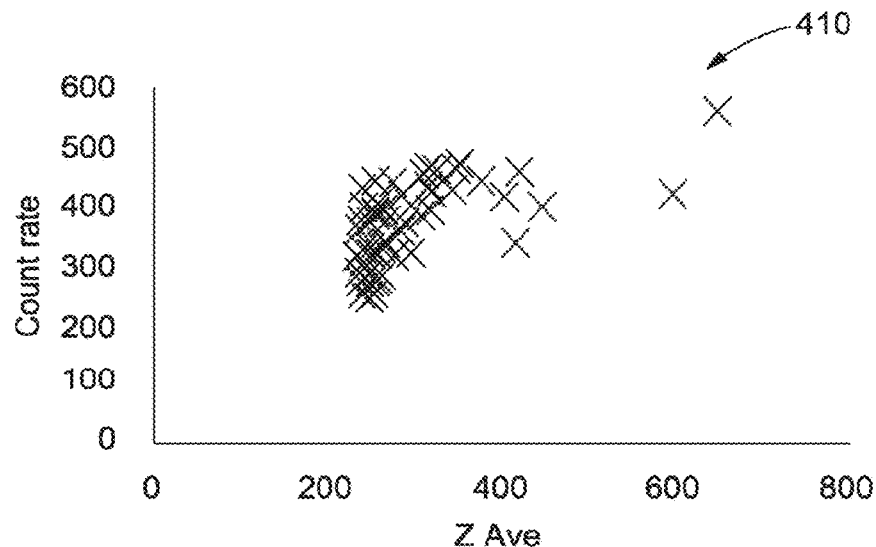
FIG. 7 shows a graph of count rate as a function of Z-average size for a sample of 220 nm latex spheres containing filter spoil (contaminants)

FIG. 7 shows a graph 410 of the mean count rate (intensity) as a function of the Z average particle size is shown for a plurality of sub-runs obtained from a measurement performed on a sample comprising 220 nm latex spheres and some filter spoil (larger size particulate contaminants). The Z average may be determined for each sub-run as defined in ISO 13321 and/or ISO 22412. One drawback of a rejection criteria based on average intensity is that it may result in the rejection of many sub-runs that the Z average indicates are associated with small particles.

Figure 8:
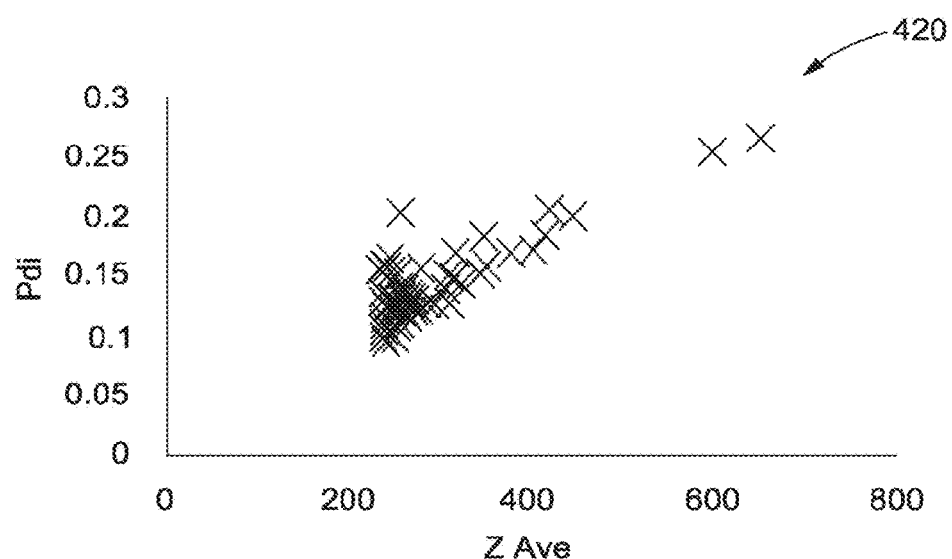
FIG. 8 shows a graph of polydispersity index (Pdi) as a function of Z-average size for the same sample used for FIG. 7.

An alternative is to reject sub-runs based on a polydispersity index (Pdi), which may be determined as defined in ISO 13321 and/or ISO 22412 from a cumulants analysis. FIG. 8 shows a graph 420 of the polydispersity index Pdi against the Z average for the same sub-run data as shown in FIG. 7. There is a stronger correlation between Z average and polydispersity index, which means that a rejection criteria based polydispersity is likely to be more selective to sub-runs dominated by larger particles.

A further alternative is to use the Z average particle size as a rejection criteria, rejecting sub-runs with a Z average particle size that exceeds a threshold value. Again, the threshold value may be determined with reference to a Z average value that is calculated from the ensemble of all sub-runs (e.g. rejecting values more than three standard deviations from a Z average for all sub-runs).

Figure 9:
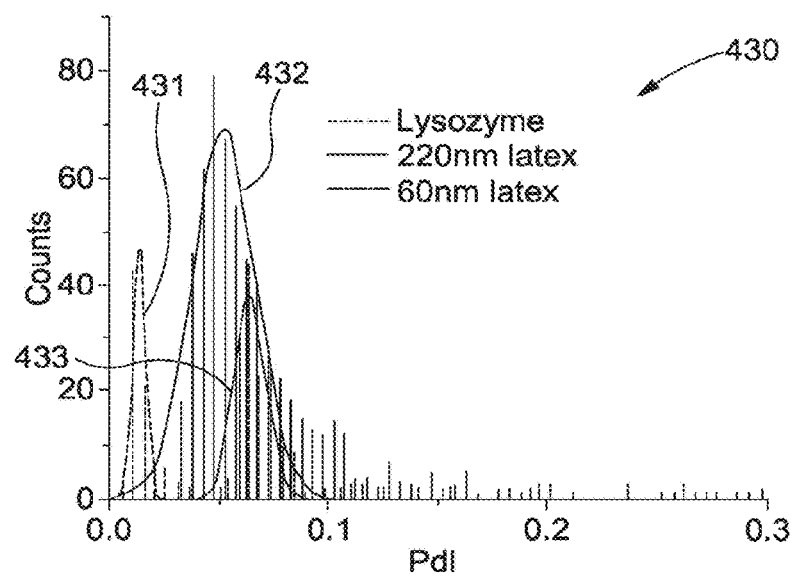
FIG. 9 shows a histogram of the polydispersity index (Pdi) for three different samples containing either dust simulant or aggregates.

FIG. 9 is a set of Pdi histograms 430 illustrating how threshold rejection criteria may be calculated for a measurement, A first, second and third histogram of Pdi values is shown, corresponding with lysozyme, 220 nm latex spheres and 60 nm latex spheres respectively. A first, second and third normal distribution 431, 432, 433 is respectively fitted to each histogram (for example, using a least squares penalty function). An average value of Pdi for each measurement and a standard deviation 6 may be determined from the normal distribution 431, 432, 433 that best fits the histogram obtained from the sub-runs of each measurement, The use of a best fit normal distribution helps to avoid skewing of the average by outlier sub-runs, which can be seen in FIG. 9 (e.g. with Pdi values greater than 0.15).

The threshold rejection criteria may an average obtained from a best fit to a histogram of sub-runs (e.g. Z average, Pdi or intensity), plus a multiple of standard deviations, for example three (or 2, 4, 5 6, etc).

Figure 10:
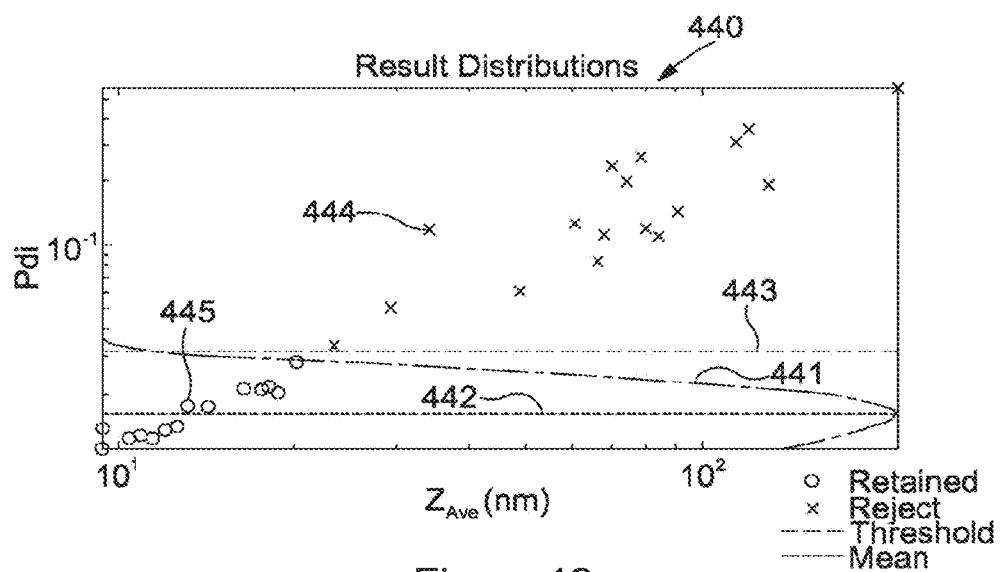
FIG. 10 shows a graph illustrating rejection/segregation criteria for sub-runs based on polydispersity index.

FIG. 10 illustrates an example rejection approach in which the rejection criteria is based on Pdi, and the threshold is three standard deviations from the average value determined from best fit normal distribution. FIG. 10 shows a graph 440 with the best fit normal distribution 441, the average Pdi 442 (derived from the best fit 441), the threshold rejection criteria 443 (the average+3σ. The retained 445 and rejected/segregated 444 sub-runs are also plotted on the same graph. Sub-runs with Pdi greater than the threshold value are rejected/segregated, and sub-runs with Pdi less than or equal to the threshold value are retained for separate analysis.

Figure 11:
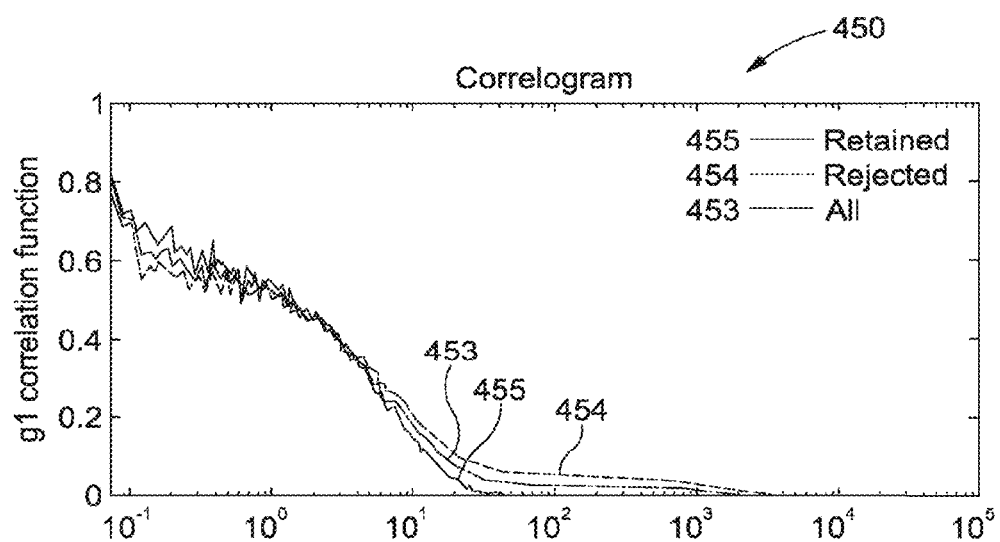
FIG. 11 shows a graph illustrating correlograms for: all sub-runs, the retained sub-runs, and the rejected/segregated sub-runs.
Figure 12:
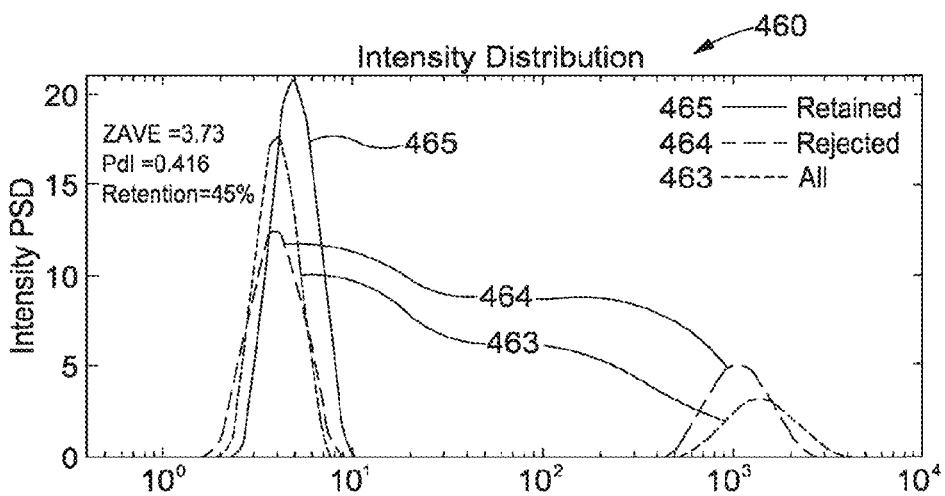
FIG. 12 shows an intensity distribution with respect to particle size for: all sub-runs, the retained sub-runs, and the rejected/segregated sub-runs.

FIG. 11 is a graph 450 showing the g1 correlation function obtained for each of: the retained sub-runs 455, the rejected/segregated sub-runs 454 and all sub-runs 453. FIG. 12 is a graph showing the intensity particle size distribution for each of: the retained sub-runs 465, the rejected/segregated sub-runs 464 and all sub-runs 463. It is clear that the retained sub-runs do not include data from the contaminant particles. The average particle size for the smaller particles (i.e. the particles of interest, excluding the contaminants) that is reported when all the sub-runs are used is different than that obtained from the retained sub-runs. The data from the retained sub-runs is more accurate, because it is not distorted by the scattering from the larger particles/contaminants. The rejected/segregated sub-runs can be used to identify characteristics of the larger (e.g. contaminant) particles. The approach of separately analysing and presenting information about the retained and rejected/segregated sub-runs provides more information to users, and removes ambiguity that may be associated with processing of light scattering data.

The use of a rejection/segregation criteria based on the distribution of a parameter (e.g. based on a standard deviation of a parameter) means that only outlying data is rejected, and that the rejection/segregation is dynamic and responsive to the sample being measured. A highly monodisperse sample with an occasional contaminant will result in a fairly narrow distribution Pdi, with the result that scattering data from contaminants will be rejected with a relatively high degree of sensitivity. At the other end of the spectrum, a highly polydisperse and variable sample may have a high standard deviation in Pdi between successive sub-runs, meaning that very little data will be rejected/segregated—the result will be a multi-modal particle size distribution, reflecting the diversity of particle sizes in the sample. This approach of determining a rejection/segregation criteria that is dynamically responsive to the analysis (e.g. based on a distribution of a parameter that is updated during the measurement) means that the measurement is robust enough to be able to accommodate a broad range of samples, and does not require the user to specify, a priori, an expected range of particles.

Figure 13:
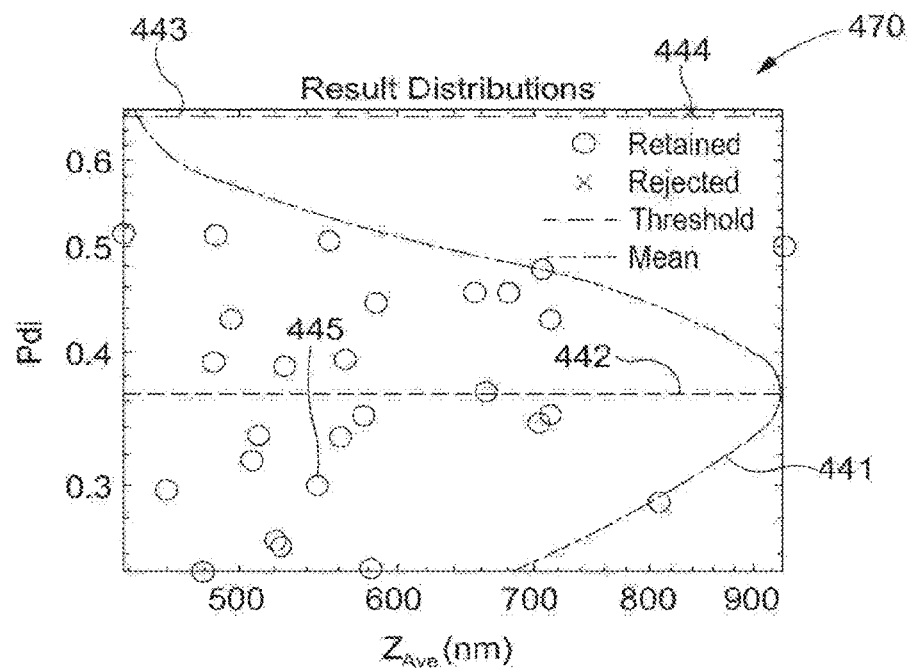
FIG. 13 shows a graph illustrating the application of a polydispersity index based rejection/segregation criteria for sub-runs in which the sample is highly polydisperse and variable.

FIG. 13 illustrates the rejection/segregation approach shown in FIG. 11, applied to a highly polydisperse and variable sample of Copper Oxide nanoparticles. For this sort of highly variable and disperse sample, a majority of sub runs are identified as non-transient and the result reported reflects the disperse nature of the sample (i.e. multi-modal/polydisperse). FIG. 13 shows a graph 470 with the best fit normal distribution 441, the average Pdi 442 (derived from the best fit 441), the threshold rejection criteria 443 (the average+3σ. The retained 445 and rejected/segregated 444 sub-runs are also plotted on the same graph. Only a single sub-run (with an unusually high Pdi) is rejected/segregated from the data set.

Although the forgoing has mainly focussed on applications in DLS, similar techniques may also be employed for SLS and ELS measurements.

In static light scattering, for applications such as molecular weight measurement, it is the magnitude of the measured scattering intensity rather than its temporal properties that are of interest, meaning that SLS measurements are also susceptible to the effects of dust within a sample.

In SLS instruments that incorporate a correlator, the same rejection process as described in DLS could be applied, and the mean intensity of the retained data used in subsequent analysis. When a correlator is not available however, rejection could still be applied by quantifying and comparing the measured scattering of each sub run, with a mean value, a drift or a spread (or some other value) being used as a rejection parameter.

Figure 14:
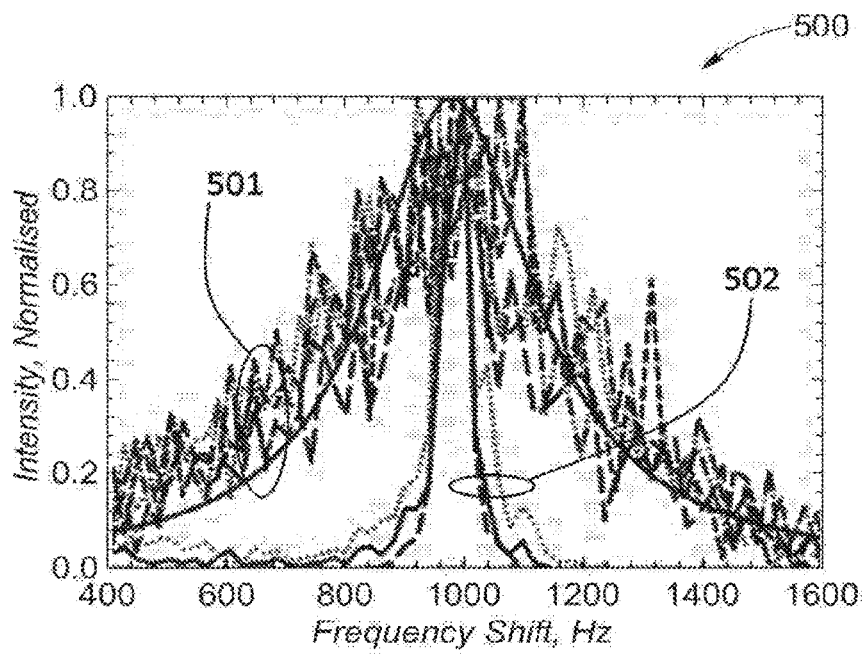
FIG. 14 is a graph or normalised intensity vs frequency shift of scattering light, showing how spectral width can be used to identify and discard outlier data.
Figure 15:
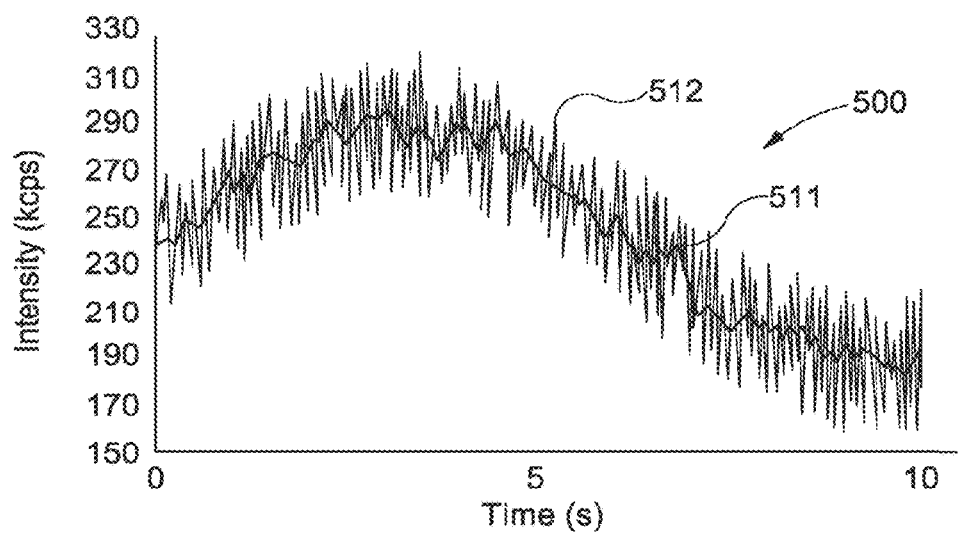
FIG. 15 is a graph of simulated count rate data showing light intensity at a scattering detector and a moving average calculated from the simulated count rate (with a 20 point window)

FIG. 14 illustrates simulated count rate data showing light intensity at a scattering detector 512, a moving average 511 calculated from the light intensity data 512 (e.g. with a 20 point window). The moving average acts as a low-pass filter, tracking the low frequency variation, while filtering out the higher frequency information of interested. Subtracting the moving average 511 from the data 512 results in the data shown in FIG. 15, in which the slow variation in intensity has been removed. Although a moving average is one type of low-pass filter that may be used to process the data, other types of filtering or smoothing operation may be used in a similar way (e.g. a digital IIR or FIR filter, or a Savitzky-Golay filter).

Electrophoretic light scattering uses an external electric field applied to a sample to induce motion in dispersed particles dependent on their charge, with this motion detected through Doppler analysis of scattered light.

As well as properties of the count rate trace, other parameters upon which rejection could be based include parameters describing the Doppler signal including spectral width.

FIG. 13 illustrates how spectral width can be used to identify and discard outlier data. The graph 500 of FIG. 13 shows a number of curves of normalised intensity vs frequency shift of scattered light. Each curve corresponds with a different measurement run (or sub-runs) of an electrophoretic measurement on samples comprising Lysozyme. The measurement runs with narrow spectral width 502 correspond with samples in which aggregates are present. The measurement runs with a broader spectral width 501 correspond with samples that do not comprise aggregates. A sample with some aggregates may be therefore analysed by taking a plurality of sub-runs and discarding those with an unusually narrow spectral width (compared with the other measurements), for example based on the distribution of measured spectral widths (e.g. a mean plus or minus a number of standard deviations).

Figure 16:
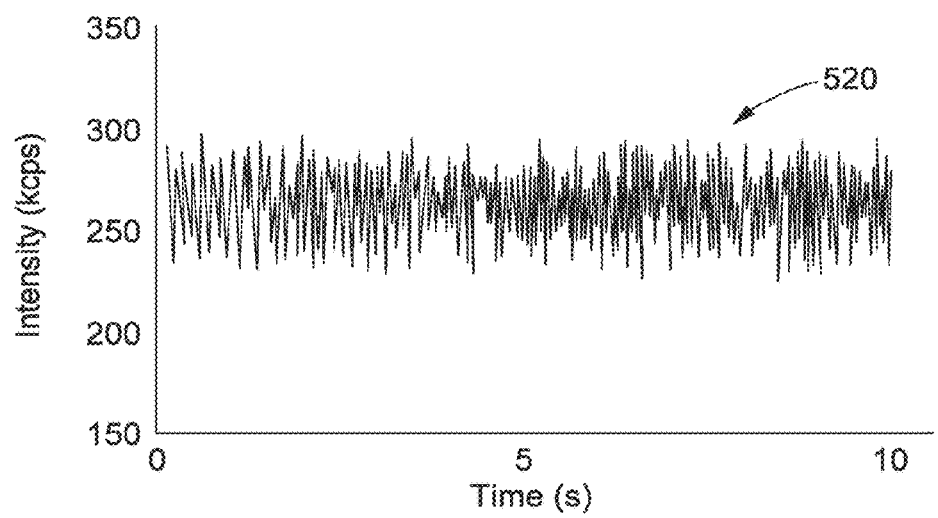
FIG. 16 is a graph of the same simulated count rate data used in FIG. 15, but with the moving average subtracted.
Figure 17:
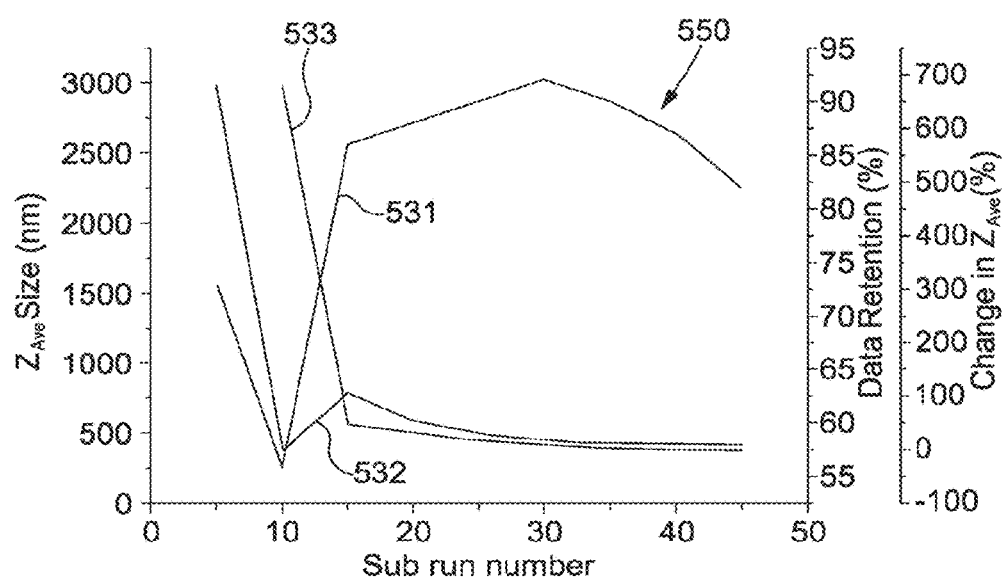
FIG. 17 is a graph illustrating the application of rejection criteria to a highly variable and polydisperse sample, showing the retention of most sub-runs.

FIG. 17 is a graph 550 illustrating how the results of an analysis may converge with increasing numbers of sub-runs. Successive sub-runs were performed, and the reported $Z_{average}$ obtained (updated every five sub-runs) from the accumulated retained data is plotted 532 in FIG. 16 on the primary y-axis (against the number of sub-runs on the x-axis). The data retention percentage, defined as the percentage of rejected/segregated sub-runs compared with the total number of sub-runs, is plotted 531 with respect to the first secondary y-axis (also determined every five sub-runs).

The change in $Z_{average}$ at each data point is plotted 533 with respect to the second secondary y-axis.

In this example data-set, the initial sub-runs include larger particles, while a significant amount of data is excluded from the first 5 sub-runs, the reported $Z_{average}$ is still relatively large. Even more data is excluded in sub-runs 6 to 10, and the reported $Z_{average}$ is lower. A more mono-modal distribution of particle sizes is detected after sub-run 10, with the result that less data is rejected, and the $Z_{average}$ begins to converge on the $Z_{average}$ for the mono-modal particle (which is likely to be the particle of interest). The $Z_{average}$ is converged to less than 1% within 45 sub-runs.

The user may be able to set a convergence criteria for triggering the end of a measurement. In the present example a less reliable measurement can be obtained by setting a $Z_{average}$ convergence tolerance of 10%, which may result in the measurement ending after around 30 sub-runs (rather than 45 sub-runs).

The use of a series of separately analysed, relatively short, sub-runs mean that the analysis can be faster, because it can be stopped early when a convergence criteria is met, at the same time as being more reliable, since transient large particles will not be allowed to impact the measurement, and the measurement may continue until sufficient reliable scattering data is obtained. The improved ability to reject inconsistent data may also allow less stringent sample preparation, or enable the analysis of samples that were previously regarded as unsuitable for analysis.

Although specific examples have been described, these are not intended to be limiting, and the skilled person will understand that further variations are possible, within the scope of the invention, which is defined by the appended claims.

The invention claimed is:

1. A method of characterising particles in a sample, comprising:
    illuminating the sample in a sample cell with a light beam, so as to produce scattered light by the interaction of the light beam with the sample;
    obtaining a time series of measurements of the scattered light from a detector;
    determining, from the time series of measurements from the detector, which measurements were taken at times when a large particle was contributing to the scattered light;
    determining a particle characteristic from the time series of measurements, including correcting for light scattered by the large particle;
    wherein correcting for light scattered by the large particle comprises determining a model of the background due to the large particle, and removing the model from the measurements.

2. The method of claim 1, further comprising determining a photon count rate signal from the time series of measurements.

3. The method of claim 2, wherein removing the model from the measurements comprises subtracting the model from the photon count rate to determine a corrected photon count rate, and determining a particle characteristic comprises determining a particle characteristic using the corrected photon count rate.

4. The method of claim 1, wherein determining a model of the background due to the large particle comprises filtering the photon count rate.

5. The method of claim 4, wherein filtering the photon count rate comprises low-pass filtering.

6. The method of claim 5, wherein the low-pass filter comprises a cut-off frequency of less than 10 Hz or less than 1 Hz.

7. The method of claim 4, wherein filtering photon count rate comprises determining a moving average of the photon count rate.

8. The method of claim 4, wherein filtering the photon count rate comprises using a Savitzky-Golay filter.

9. The method of claim 4, wherein filtering the photon count rate comprises using a digital IIR or FIR filter.

10. The method of claim 1, wherein the particle characteristic is one of a particle size distribution, an electrophoretic mobility, a magnetophoretic mobility and a microrheological property.

11. An apparatus for characterising particles comprising: a light source, a sample cell, a detector and a processor; wherein
    the light source is operable to illuminate a sample within the sample cell with a light beam so as to produce scattered light by interactions of the light beam with the sample;
    the detector is configured to detect the scattered light and produce a time series of measurements;
    the processor is configured to:
        receive the time series of measurements, and
        determine, from the time series of measurements, which measurements were taken at times when a large particle was contributing to the scattered light;
        determine a particle characteristic from the time series of measurements, including correcting for light scattered by the large particle;
    wherein correcting for light scattered by the large particle comprises determining a model of the light scattered by the large particle, and removing the model from the measurements.

12. The apparatus of claim 11, wherein the processor is configured to determine a photon count rate signal from the time series of measurements.

13. The apparatus of claim 12, wherein removing the model from the measurements comprises subtracting the model from the photon count rate to determine a corrected photon count rate, and determining a particle characteristic comprises determining a particle characteristic using the corrected photon count rate.

14. The apparatus of claim 11, wherein determining a model of the background due to the large particle comprises filtering the photon count rate.

15. The apparatus of claim 14, wherein filtering the photon count rate comprises low-pass filtering.

16. The apparatus of claim 15, wherein the low-pass filter comprises a cut-off frequency of less than 10 Hz or less than 1 Hz.

17. The apparatus of claim 14, wherein filtering the photon count rate comprises determining a moving average of the photon count rate.

18. The apparatus of claim 14, wherein filtering the photon count rate comprises using a Savitzky-Golay filter.

19. The apparatus of claim 14, wherein filtering the photon count rate comprises using a digital IIR or FIR filter.

20. The apparatus of claim 11, wherein the particle characteristic is one of a particle size distribution, an electrophoretic mobility, a magnetophoretic mobility and a microrehological property.

* * * * *